United States Patent
Cho et al.

(10) Patent No.: US 11,819,566 B2
(45) Date of Patent: Nov. 21, 2023

(54) COMPOSITION FOR IMPROVING SKIN TRANSPARENCY AND REDUCING DULLNESS

(71) Applicant: AMOREPACIFIC CORPORATION, Seoul (KR)

(72) Inventors: Gayoung Cho, Yongin-si (KR); Lee Kyoung Kwon, Yongin-si (KR); Sowoong Choi, Yongin-si (KR); Nok Hyun Park, Yongin-si (KR); Eun Soo Lee, Yongin-si (KR); Byungfhy Suh, Yongin-si (KR); Seonga Cho, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 505 days.

(21) Appl. No.: 17/271,790

(22) PCT Filed: Aug. 26, 2019

(86) PCT No.: PCT/KR2019/010845
§ 371 (c)(1),
(2) Date: Feb. 26, 2021

(87) PCT Pub. No.: WO2020/045921
PCT Pub. Date: Mar. 5, 2020

(65) Prior Publication Data
US 2021/0338565 A1    Nov. 4, 2021

(30) Foreign Application Priority Data
Aug. 27, 2018  (KR) .................. 10-2018-0100595

(51) Int. Cl.
*A61K 8/9789* (2017.01)
*A61K 8/9767* (2017.01)
*A61Q 19/02* (2006.01)

(52) U.S. Cl.
CPC .......... *A61K 8/9789* (2017.08); *A61K 8/9767* (2017.08); *A61Q 19/02* (2013.01); *A61K 2800/5922* (2013.01)

(58) Field of Classification Search
None
See application file for complete search history.

(56) References Cited

FOREIGN PATENT DOCUMENTS

| | | |
|---|---|---|
| CN | 106798713 A | 6/2017 |
| JP | 2004-509912 A | 4/2004 |
| JP | 2006-273811 A | 10/2006 |
| JP | 2012-201637 A | 10/2012 |
| JP | 2013-144654 A | 7/2013 |
| KR | 10-2005-0022142 A | 3/2005 |
| KR | 10-2005-0108541 A | 11/2005 |
| KR | 10-2011-0041616 A | 4/2011 |
| KR | 10-1039531 B1 | 6/2011 |
| KR | 10-2011-0087379 A | 8/2011 |
| KR | 10-2012-0087716 A | 8/2012 |
| KR | 10-1427027 B1 | 8/2014 |
| KR | 10-2015-0057667 A | 5/2015 |
| KR | 10-2017-0137405 A | 12/2017 |
| KR | 10-2017-0137432 A | 12/2017 |

OTHER PUBLICATIONS

International Search Report PCT/KR2019/010845, dated Dec. 2, 2019.

*Primary Examiner* — Danah Al-Awadi
(74) *Attorney, Agent, or Firm* — Merchant & Gould P.C.

(57) ABSTRACT

In the present specification, a composition for improving skin transparency and a composition for reducing skin dullness are disclosed. The composition contains a mixed extract of *Rosa multiflorae* Fructus, black sesame, plum, quince, and pine nut as an active ingredient, wherein the *Rosa multiflorae* Fructus and black sesame may be germinated. Also, the composition has the effect of improving skin that has become dull due to the effects of aging, the external environment, stress, etc., so that the skin is made clear and transparent.

14 Claims, 4 Drawing Sheets

COMPOSITION FOR IMPROVING SKIN TRANSPARENCY AND REDUCING DULLNESS

CROSS-REFERENCE TO RELATED APPLICATIONS

This application is a National Stage Application of PCT/KR2019/010845, filed Aug. 26, 2019, which claims benefit of priority to Serial No. 10-2018-0100595, filed Aug. 27, 2018 in the Republic of Korea and which applications are incorporated herein by reference. To the extent appropriate, a claim of priority is made to each of the above disclosed applications.

TECHNICAL FIELD

Disclosed are a composition for improving skin transparency and a composition for improving skin dullness.

BACKGROUND ART

The trend of conventional whitening cosmetics aims at white skin by simply removing melanin pigments which are abnormally expressed; however, recently, demands of products having efficacy such as transparency, in addition to simply aiming at white skin, have been increased. However, existing whitening raw materials having a function of inhibiting melanin synthesis cannot sufficiently meet such demands of customers.

Recently, studies on factors which influence on skin color or skin transparency, other than melanin, have been actively conducted. It has been actually found that several factors of adjusting scattering and refraction of light in skin, in addition to simple skin color, act complexly to determine skin transparency. For example, melanin, skin uniformity, an amount of moisture, hemoglobin, etc. have been known as main influencing factors. As such several factors act complexly, skin transparency varies depending on the quantity of light transmitted through skin itself.

CITATION LIST

Patent Literature

[Patent Literature 1]
KR 10-2015-0057667 A
[Patent Literature 2]
JP 2004-509912 A

SUMMARY OF INVENTION

Technical Problem

According to one aspect of the present disclosure, an object of the present disclosure is to provide a composition for improving skin transparency, comprising a mixture extract from *Rosa multiflora* fruit, black sesame, *Prunus mume* fruit, quince and pine nut, as an active ingredient.

According to another aspect of the present disclosure, an object of the present disclosure is to provide a composition for improving skin dullness, comprising a mixture extract from *Rosa multiflora* fruit, black sesame, *Prunus mume* fruit, quince and pine nut, as an active ingredient.

Solution to Problem

According to one aspect of the present disclosure, the technology disclosed in the specification of the present disclosure provides a composition for improving skin transparency, comprising a mixture extract from *Rosa multiflora* fruit, black sesame, *Prunus mume* fruit, quince and pine nut, as an active ingredient.

According to another aspect of the present disclosure, the technology disclosed in the specification of the present disclosure provides a composition for improving skin dullness, comprising a mixture extract from *Rosa multiflora* fruit, black sesame, *Prunus mume* fruit, quince and pine nut, as an active ingredient.

In one exemplary embodiment, said *Rosa multiflora* fruit and black sesame may be germinated *Rosa multiflora* fruit and germinated black sesame.

In one exemplary embodiment, said germinated *Rosa multiflora* fruit, germinated black sesame, *Prunus mume* fruit, quince and pine nut may be mixed at weight ratios of 10 to 30:20 to 40:10 to 25:15 to 30:15 to 30, respectively, and then extracted.

In one exemplary embodiment, said extract may be a solvent extract from at least one of water and lower alcohols having 1 to 4 carbon atoms.

In one exemplary embodiment, said extract may be an ethanol extract.

In one exemplary embodiment, said composition may comprise 0.001 to 20 wt. % of said mixture extract.

In one exemplary embodiment, said composition may be a cosmetic composition.

In one exemplary embodiment, said composition may be in a skin, lotion, essence, cream, gel or pack formulation.

In one exemplary embodiment, said skin transparency may be a ratio of transmitted light to incident light on a skin surface.

In one exemplary embodiment, when measuring skin subsurface reflection values before and after the use of said composition at incident angle 60° and reflection angle 60° on the skin surface, the increase rate of the skin subsurface reflection value may be 2% or more as compared to the skin subsurface reflection value before the use of the composition.

In one exemplary embodiment, said composition may inhibit the generation of a substance exhibiting autofluorescence under the fluorescence conditions of 340 nm of excitation light and 440 nm of emission light.

Advantageous Effects of Invention

According to one aspect of the present disclosure, the technology disclosed in the specification of the present disclosure has an effect of providing a composition for improving skin transparency and dullness, comprising a mixture extract from *Rosa multiflora* fruit, black sesame, *Prunus mume* fruit, quince and pine nut, as an active ingredient.

The composition disclosed in the specification of the present disclosure has an effect of improving skin, which has become dark and dull by aging or by external environments or influences such as stress, to be clean and transparent.

DESCRIPTION OF EMBODIMENTS

Figure 1:
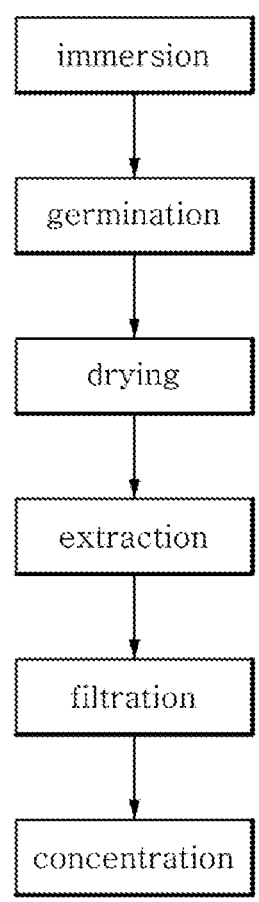
FIG. 1 shows a process for preparing a mixture extract according to one embodiment of the present disclosure.

Hereinafter, the present disclosure will be explained in detail.

According to one aspect, the technology disclosed in the specification of the present disclosure provides a composition for improving skin transparency, comprising a mixture extract from *Rosa multiflora* fruit, black sesame, *Prunus mume* fruit, quince and pine nut, as an active ingredient.

According to another aspect, the technology disclosed in the specification of the present disclosure provides a method for improving skin transparency, comprising applying an effective amount of a mixture extract from *Rosa multiflora* fruit, black sesame, *Prunus mume* fruit, quince and pine nut for improving skin transparency to a subject in need thereof.

According to another aspect, the technology to a disclosed in the specification of the present disclosure provides a mixture extract from *Rosa multiflora* fruit, black sesame, *Prunus mume* fruit, quince and pine nut, for improving skin transparency.

According to another aspect, the technology disclosed in the specification of the present disclosure provides a non-therapeutic use of a mixture extract from *Rosa multiflora* fruit, black sesame, *Prunus mume* fruit, quince and pine nut, for improving skin transparency.

According to another aspect, the technology disclosed in the specification of the present disclosure provides a use of a mixture extract from *Rosa multiflora* fruit, black sesame, *Prunus mume* fruit, quince and pine nut, in manufacturing a composition for improving skin transparency.

According to one another aspect, the technology described in the specification of the present disclosure provides a composition for improving skin dullness, comprising a mixture extract from *Rosa multiflora* fruit, black sesame, *Prunus mume* fruit, quince and pine nut, as an active ingredient.

According to another aspect, the technology disclosed in the specification of the present disclosure provides a method for improving skin dullness, comprising applying an effective amount of a mixture extract from *Rosa multiflora* fruit, black sesame, *Prunus mume* fruit, quince and pine nut for improving skin dullness to a subject in need thereof.

According to another aspect, the technology disclosed in the specification of the present disclosure provides a mixture extract from *Rosa multiflora* fruit, black sesame, *Prunus mume* fruit, quince and pine nut, for improving skin dullness.

According to another aspect, the technology disclosed in the specification of the present disclosure provides a non-therapeutic use of a mixture extract from *Rosa multiflora* fruit, black sesame, *Prunus mume* fruit, quince and pine nut, for improving skin dullness.

According to another aspect, the technology disclosed in the specification of the present disclosure provides a use of a mixture extract from *Rosa multiflora* fruit, black sesame, *Prunus mume* fruit, quince and pine nut, in manufacturing a composition for improving skin dullness.

In one exemplary embodiment, said mixture extract from *Rosa multiflora* fruit, black sesame, *Prunus mume* fruit, quince and pine nut, or said composition may be applied to a subject in one or more forms of a pharmaceutical composition, a skin external preparation composition, a food composition and a cosmetic composition.

In one exemplary embodiment, said mixture extract from *Rosa multiflora* fruit, black sesame, *Prunus mume* fruit, quince and pine nut, or said composition may be applied to skin of the subject.

In one exemplary embodiment, said application may be administering or applying to the subject.

In the specification of the present disclosure, active ingredient means an ingredient which exhibits a desired activity alone or can exhibit a desired activity in combination with a carrier, etc. which has no activity itself.

In the specification of the present disclosure, skin transparency means a ratio of transmitted light to incident light on a skin surface. As incident light is scattered on a skin surface, some of light is scattered and then the remaining is transmitted into skin, and the light transmitted (transmitted light) is reflected inside the skin and then exits. As the quantity of light reflected inside the skin (diffused reflection) is increased, skin transparency is increased.

In one exemplary embodiment, said skin transparency is a ratio of transmitted light to incident light on a skin surface, wherein said transmitted light may be measured with a subsurface reflection value reflected inside the skin.

In one exemplary embodiment, when measuring the skin subsurface reflection values before and after the use of said mixture extract or said composition at incident angle 60° and reflection angle 60° on the skin surface, the increase rate of the skin subsurface reflection values may be 2% or more, 3% or more, 4% or more, 5% or more or 6% or more as compared to the skin subsurface reflection values before the use of the mixture extract or composition.

In one another exemplary embodiment, when measuring the skin subsurface reflection values before and after the use of said mixture extract or said composition at incident angle 60° and reflection angle 60° on the skin surface, the increase rate of the skin subsurface reflection values may be 2% to 12%, 2% to 10% or 2% to 8% as compared to the skin subsurface reflection values before the use of the mixture extract or composition.

In one exemplary embodiment, the skin subsurface reflection values may be measured by Radioscan™ (True system, Korea).

In the specification of the present disclosure, skin dullness may mean the state where brightness and chroma of skin are degraded, and thereby, skin tone is darkened or partially has dark and deep color, so skin tone is not uniform. Skin dullness is caused by various complex factors such as physiological factors, genetic factors, environmental factors, etc.

In one exemplary embodiment, said mixture extract or said composition may, when applied to skin, inhibit the generation of a substance exhibiting autofluorescence under the fluorescence conditions of 340 nm of excitation light and 440 nm of emission light or reduces the substance.

Said mixture extract or said composition comprising the mixture extract according to the specification of the present disclosure has an effect of making dull skin clean and increasing skin transparency.

In one exemplary embodiment, use of said mixture extract or said composition may be applying said mixture extract or said composition on skin for 2 weeks or more, 4 weeks or more or from 4 week to 8 week.

In one exemplary embodiment, use of said mixture extract or said composition may be applying said mixture extract of said composition on skin twice a day.

In the specification of the present disclosure, the mixture extract may mean a mixture of an extract extracted from one extracting raw material, a mixture of an extract extracted by mixing one or more extracting raw materials, or an extract extracted by mixing five extracting raw materials. Said extracting raw materials refer to Rosa multiflora fruit, black sesame, Prunus mume fruit, quince and pine nut.

In one exemplary embodiment, said Rosa multiflora fruit and black sesame may be germinated Rosa multiflora fruit and germinated black sesame.

Rosa multiflora fruit refers to a fruit of Rosa multiflora Thunberg which commonly grows in the mountains.

In one exemplary embodiment, said germinated Rosa multiflora fruit, germinated black sesame, Prunus mume fruit, quince and pine nut are preferably mixed at the weight ratios of 10 to 30:20 to 40:10 to 25:15 to 30:15 to 30, respectively, and then extracted in aspect of efficacy of improving skin transparency and improving skin dullness.

In one exemplary embodiment, said extract refers not only to a crude extract but also to processed articles of the crude extracts, for example, all forms of extracts by additional processing such as drying, concentration, fraction, purification, fermentation, suspension, etc., and said additional processing may include one or more processing. For example, fractional extracts include all of fractions obtained by suspending said crude extract in a certain solvent and then mixing it with a solvent having a different polarity and refining, and fractions obtained by dividing said crude extract into fractions with a sequential solvent. In addition, fractions obtained by various purification methods additionally conducted, such as a separation using ultrafiltration membranes having constant molecular weight cut-off values, a separation by various chromatography (which are manufactured for separation depending on size, charge, hydrophobicity or amphipathy) are also included in the extract of the present disclosure.

In one exemplary embodiment, any method for preparing an extract can be applied according to typical methods such as a hot water extraction method, a dipping extraction method, a steam distillation method, a chilling extraction method, a reflux cooling extraction method, a supersonic extraction method, a supercritical extraction method, a subcritical extraction method, a solvent extraction method, an elution method, a compression method, a high-temperature extraction method, a high-pressure extraction method, an extraction method using an absorbent resin comprising XAD and HP-20, or fermentation or natural fermentative metabolites using microorganisms, in consideration of the extracting degree or storing degree of an active ingredient. The number of extractions may be 1 to 5 times, and after extracting, methods such as a distillation under reduced pressure, concentration under reduced pressure, freeze-drying or spraying-drying, etc. may be additionally performed.

In one exemplary embodiment, said extract may be extracted with one or more solvents selected from a group consisting of water, anhydrous or hydrated lower alcohols having 1 to 4 carbon atoms (for example, methanol, ethanol, propanol, butanol, etc.), ethylene, acetone, hexane, ether, chloroform, ethyl acetate, butyl acetate, dichloromethane, N,N-dimethylformamide (DMF), methylene chloride, dimethylsulfoxide (DMSO), glycerin, butylene glycol, propylene glycol, dipropylene glycol, methylenechloride, diethylether and a mixture thereof.

In one exemplary embodiment, said extract may be a solvent extract from at least one of water and lower alcohols having 1 to 4 carbon atoms.

In one exemplary embodiment, said extract may be an ethanol extract. Said ethanol extract means an extract extracted using an extracting solvent consisting of ethanol only or an extracting solvent in which water and ethanol are mixed.

In one exemplary embodiment, said extract may be prepared by immersing Rosa multiflora fruit and black sesame into water and germinating it; and mixing the germinated Rosa multiflora fruit and the germinated black sesame with Prunus mume fruit, quince and pine nut and extracting it.

In one exemplary embodiment, said immersion may be carried out for 2 to 20 hours.

In one exemplary embodiment, said germination may be carried out at room temperature, for example, 15 to 25° C. or 20 to 25° C.

In one exemplary embodiment, said germination may be carried out for 30 to 60 hours.

In one exemplary embodiment, said extract may be extracted by an ethanol solvent having a concentration of 30 to 80% (v/v). In one another exemplary embodiment, said extract may be extracted with an ethanol solvent having a concentration of 30% or more, 35% or more, 40% or more, 45% or more, 50% or more, 55% or more, 60% or more, 65% or more, 70% or more, or 75% or more, and 80% or less, 75% or less, 70% or less, 65% or less, 60% or less, 55% or less, 50% or less, 45% or less, 40% or less or 35% or less (v/v).

In one exemplary embodiment, said extract may be extracted at 15 to 85° C. In one another exemplary embodiment, said extract may be extracted at a temperature of 15° C. or more, 25° C. or more, 35° C. or more, 45° C. or more, 55° C. or more, 65° C. or more, or 75° C. or more, and 85° C. or less, 75° C. or less, 65° C. or less, 55° C. or less, 45° C. or less, 35° C. or less or 25° C. or less.

In one exemplary embodiment, said extraction time may be 1 hour or longer, or from 1 to 24 hours.

In one exemplary embodiment, said composition may comprise 0.001 to 20 wt. % of the mixture extract. In one another exemplary embodiment, said composition may comprise 0.001 wt. % or more, 0.005 wt. % or more, 0.01 wt. % or more, 0.05 wt. % or more, 0.1 wt. % or more, 0.5 wt. % or more, 1 wt. % or more, 1.5 wt. % or more, 2 wt. % or more, 2.5 wt. % or more, 3 wt. % or more, 3.5 wt. % or more, 4 wt. % or more, 4.5 wt. % or more or wt. % or more and 20 wt. % or less, 15 wt. % or less, 10 wt. % or less, 5 wt. % or less or 1 wt. % or less of the mixture extract, so that the composition can provide the effect of improving excellent skin transparency and dullness.

In one exemplary embodiment, said composition may comprise the mixture extract at a concentration of 10 ppm, 15 ppm, 20 ppm, 25 ppm, 30 ppm, 35 ppm, 40 ppm, 45 ppm or 50 ppm or more. Said composition may preferably comprise the mixture extract at a concentration of 25 ppm, 30 ppm, 35 ppm, 40 ppm, 45 ppm or 50 ppm or more.

In one exemplary embodiment, said composition may be a pharmaceutical composition.

In one exemplary embodiment, the formulation of said pharmaceutical composition may be solution, suspension, liquid, gel, drop, suppository, cream, ointments, patch, pad or spray, but this is not limited thereto. The formulation can be easily prepared according to typical methods in the pertinent field, and excipient, water-dispersible agent, emulsifier, suspension, salt or buffer for osmotic pressure control, coloring, spice, stabilizer, antimicrobial agent, preservative or other commercial auxiliaries can be properly used.

In addition, said pharmaceutical composition can be administered by an oral administration, a parenteral administration, a rectal administration, a topical administration, transdermal administration, an intravenous administration, an intramuscular administration, an intraabdominal administration, a subcutaneous administration, etc. depending on a desired method, and the active ingredients of the pharmaceutical composition may vary depending on age, gender, weight, a pathology and its severity of a subject to be administered, an administration route or a prescriber's decision. The determination of a dose based on such factors is made within the level of a person having a skill in the art, and daily doses thereof may be for example 0.001 mg/g/day to 100 mg/g/day, more specifically, 0.5 mg/g/day to 50 mg/g/day, but this is not limited thereto.

In one exemplary embodiment, said composition may be a skin external preparation composition, wherein the skin external preparation composition includes all preparations applied on the outside of skin, including various formulations of medicines. For example, said composition may be in a formulation such as ointment, lotion, gel, cream, spray, suspension, emulsion, patch, etc., but this is not limited thereto.

In one exemplary embodiment, said skin external preparation composition may further contain, in addition to the active ingredient according to the specification of the present disclosure, pharmaceutical adjuvants such as antimicrobial agent, stabilizer, water-dispersible agent or emulsifier, salt and/or buffer for osmotic pressure control, etc. and other therapeutically useful materials.

In one exemplary embodiment, said composition may be a fool composition.

In the specification of the present disclosure, the food composition may provide various forms of food additives or functional food. More specifically, it can be processed as leached tea, liquid tea, beverage, fermented milk, cheese, yogurt, juice, probiotics or health supplement food, comprising said composition, and the composition can be used in other forms of various food additives.

In addition, said food composition may further comprise other ingredients, etc. which give a synergistic effect to the main effect within the range that does not damage the main effect for which the active ingredient is desired. For example, for improving physical properties, the composition may further comprise additives such as perfume, color, sterilizer, antioxidant, preservative, moisturizer, thickener, mineral salt, emulsifier or synthetic polymer, etc. In addition, the composition may further comprise auxiliary ingredients such as water-soluble vitamin, oil-soluble vitamin, polymer peptide, polymer polysaccharide or seaweed extract, etc. Said components can be properly selected and blended depending on formulations or purposes of use by a person having skill in the art without any difficulties, and the amounts of addition can be selected within the range that does not damage the objects and effect of the present disclosure. For example, the amounts of said ingredients added may be in the range of 0.001 to 5 wt. %, or 0.01 to 3 wt. %, on the basis of the total weight of the composition.

In one exemplary embodiment, said composition may be a cosmetic composition.

Said cosmetic composition may further comprise, in addition to the mixture extract, functional additives and components which are comprised in typical cosmetic compositions. Said functional additives include components selected from a group consisting of water-soluble vitamin, oil-soluble vitamin, polymer peptide, polymer polysaccharide, sphingolipid, and seaweed extract. The examples of other components blended include oil, moisturizer, emollient, surfactant, organic and inorganic pigments, organic powder, ultraviolet absorbent, antimicrobial agent, sterilizer, antioxidant, herb extract, pH adjuster, alcohols, color, perfume, blood circulating promoter, cooling agent, antiperspirant, purified water, etc.

The formulations of said cosmetic composition are not particularly limited, and can be properly selected depending on a desired object. For example, the cosmetic composition can be prepared in one or more formulations selected from a group consisting of skin lotion, skin softener, skin toner, astringent, lotion, milk lotion, moisture lotion, nourishing lotion, massage cream, hand cream, foundation, essence, nourishing essence, pack, soap, cleansing foam, cleansing lotion, cleansing cream, body lotion and body cleanser, but this is not limited thereto.

In case where the formulation of the present disclosure is paste, cream or gel, as a carrier ingredient, animal fiber, vegetable fiber, wax, paraffin, starch, tragacanth, cellulose derivative, polyethylene glycol, silicon, bentonite, silica, talc or zinc oxide, etc. can be used.

In case where the formulation of the present disclosure is powder or spray, as a carrier ingredient, lactose, talc, silica, aluminum hydroxide, calcium silicate or poly amide power can be used. In particular, in case where the formulation is spray, it may further comprise propellants such as chlorofluorohydrocarbons, propane/butane or dimethyl ether.

In case where the formulation of the present disclosure is a solution or emulsion, as a carrier ingredient, solvent, solvating agent or demulsifier is used, and the examples thereof include, for example, water, ethanol, isopropanol, ethyl carbonate, ethyl acetate, benzyl alcohol, benzyl benzoate, propylene glycol, 1,3-butylglycol oil, glycerol aliphatic ester, fatty acid ester of polyethylene glycol or sorbitan.

In case where the formulation of the present disclosure is a suspension, as a carrier ingredient, liquid diluent such as water, ethanol or propylene glycol, suspension such as ethoxylated isostearyl alcohol, polyoxyethylene sorbitol esters and polyoxyethylene sorbitan esters, microcrystalline cellulose, aluminum metahydroxide, bentonite, agar or tragacanth, etc. can be used.

In case where the formulation of the present disclosure is a surfactant-containing cleansing, as a carrier ingredient, fatty alcohol sulfate, fatty alcohol ether sulfate, sulfosuccinic acid monoester, isethionate, imidazolinium derivatives, methyltaurate, sarcosinate, fatty acid amid ether sulfate, alkyl amidobetains, fatty acid alcohol, fatty acid glycerides, fatty acid diethanolamide, vegetable oil, rynoline derivatives or ethoxylated glycerol fatty acid esters, etc. can be used.

EMBODIMENTS

Hereinafter, the present disclosure will be explained in more detail through examples. These examples are only to exemplify the present disclosure, and it is obvious to a person having ordinary knowledge in this pertinent art that the scope of the present disclosure is not limited to these examples.

EXAMPLES

Example 1. Preparation of a Mixture Extract

*Rosa multiflora* fruit and black sesame were immersed into water, respectively, and were taken out of the water and germinated at room temperature, and then dried. After drying, the germinated *Rosa multiflora* fruit and germinated black sesame were mixed with *Prunus mume* fruit, quince and pine nut, and then extracted, filtered and concentrated at 50 to 55° C. using an extracting solvent of 70% (v/v) ethanol to prepare a mixture extract (refer to FIG. 1).

Test Example 1. Cytotoxicity Evaluation

In order to evaluate cytotoxicity of the mixture extract prepared in Example 1, a CCK-8 assay was conducted for human fibroblast. The CCK-8 assay was conducted according to the method typically carried out.

The test was conducted with n=4 per group, and the human fibroblast (Human Dermal Fibroblast neonatal: HDFn) was cultured under the condition of 37° C., 5% $CO_2$ incubator in a DMEM (Dulbecco's Modified Eagle's Medium) medium containing 10% fetal bovine serum (FBS, Gibco).

Figure 2:
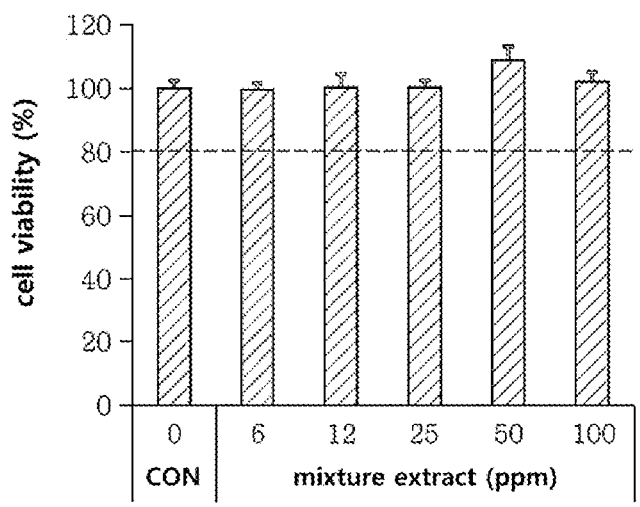
FIG. 2 shows the evaluation result of cytotoxicity of the mixture extract according to one embodiment of the present disclosure.

The mixture extract of Example 1 was treated with the fibroblast for 18 hours at a concentration of 6 to 100 ppm, and the cell survival rate thereof was compared with the survival rate of control (CON) in which the mixture extract was not treated. The result is shown in FIG. 2. As the result, at all concentrations at which the mixture extract was treated, cytotoxicity was not exhibited, and thus, it was confirmed that the mixture extract of Example 1 has no cytotoxicity.

Test Example 2. Evaluation of Efficacy of Improving Skin Dullness

The efficacy of the mixture extract of Example 1 on improving skin dullness was evaluated using Aminoguanidine (AG), which has the efficacy of improving pigmentation, as a positive control. According to Patent Literature JP 2004-509912 A, aminoguanidine is an active ingredient which has been known as improving pigmentation, skin dullness, the contents of which in its entirety are herein incorporated by reference.

Fibroblast (Human Dermal Fibroblast neonatal: HDFn) was put into a 48-well plate to prepare a collagen matrix, and treated with a specimen, and then, the fibroblast was cultured in the collagen matrix for 7 days (culturing conditions; 37° C., 5% $CO_2$ incubator). The treatment with the specimen was classified into a group treated with 30 mM of ribose (Sigma aldrich, Cat No. R9629) alone, a group treated with 30 mM of ribose and 20 mM of aminoguanidine (Sigma aldrich, Cat No. A7009), and a group treated with 30 mM of ribose and 12 to 50 ppm of the mixture extract of Example 1. After 7 days from the treatment of the fibroblast with the specimen, the efficacy of improving skin dullness was compared by measuring autofluorescence values at a certain wavelength specifically reacting to a substance reduced by the treatment with aminoguanidine which has the efficacy of improving skin dullness. The autofluorescence was measured using a microplate reader (BioTek product) under the fluorescence measuring conditions of 340 nm of excitation and 440 nm of emission.

Figure 3:
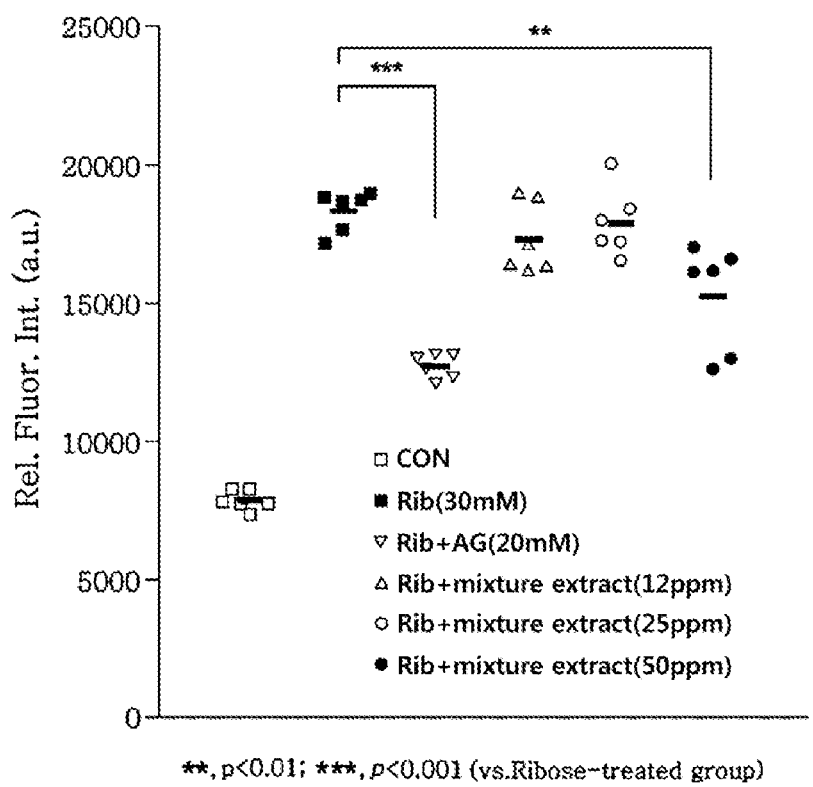
FIG. 3 shows the evaluation result of efficacy of the mixture extract on improving skin dullness according to one embodiment of the present disclosure (\*\*, p<0.01; \*\*\*, p<0.001 vs. Ribose-treated group).

The test was conducted with n=6 per group, and as shown in FIG. 3, each of the test results is indicated with symbols, and the average values for each group are indicated with solid lines (-).

As the result of culturing the fibroblast in the collagen matrix by treating with ribose (Rib) as an excitation source, it was confirmed that ribose increased the generation of a substance which exhibits autofluorescence at 340 nm of excitation and 440 nm of emission. To be specific, the autofluorescence strength of ribose was increased by about 132% as compared to a non-treated group (Control: CON). In addition, aminoguanidine, which has the efficacy of improving skin dullness, reduced the autofluorescence strength, which was increased by ribose, by about 54.0%. Thereby, in the specification of the present disclosure, the substance which exhibits autofluorescence at 340 nm of excitation and 440 nm of emission is called "a skin browning ingredient."

As shown in FIG. 3, it was confirmed that even when treating the fibroblast with the mixture extract of Example 1, the autofluorescence value, which was increased by ribose, was reduced. Thus, it can be verified that the mixture extract of Example 1 has the efficacy of inhibiting the generation of a skin browning ingredient and improving skin dullness, like aminoguanidine. In addition, it was also confirmed that when treating the fibroblast with the mixture extract of Example 1 at a concentration exceeding 25 ppm, the reduction rate of skin browning ingredients increased, thereby confirming excellent effect in improving skin. When treating the fibroblast with the mixture extract at a concentration of 50 ppm, the autofluorescence value was reduced by about 29.4% as compared with the group treated with ribose alone.

Test Example 3. Evaluation of Efficacy of Improving Skin Transparency

A test product containing the mixture extract of Example 1 was prepared according to the composition of Table 1, and then the efficacy of improving skin transparency was evaluated.

TABLE 1

| Blending ingredients | Content (wt. %) |
| --- | --- |
| Mixture extract of Example 1 | 0.5 |
| Glycerin | 3.0 |
| Butylene glycol | 2.0 |
| Propylene glycol | 2.0 |
| Carboxyvinyl polymer | 0.1 |
| Cetyl octanoate | 1.0 |
| Polysorbate 60 | 0.4 |
| Ethanol | 10.0 |
| Xanthan gum | 0.07 |
| Preservative, color, spice | proper amount |
| Purified water | balance |
| Total | 100 |

The test was conducted for 21 women in their 30s to 50s, and they applied the test product on the entire face twice a day for 8 weeks. In addition, the subsurface reflection values were analyzed by measuring the skin transparency of the front site of the right cheek at an incidence angle of 60° and a reflection angle of 60° under the same environmental conditions using Radioscan™ (True system, Korea), before the use of the product, after 4 weeks, and after 8 weeks, respectively. The skin having high transparency exhibits high light reflection (subsurface reflection) inside the skin when light is inclined into the skin.

Figure 4:
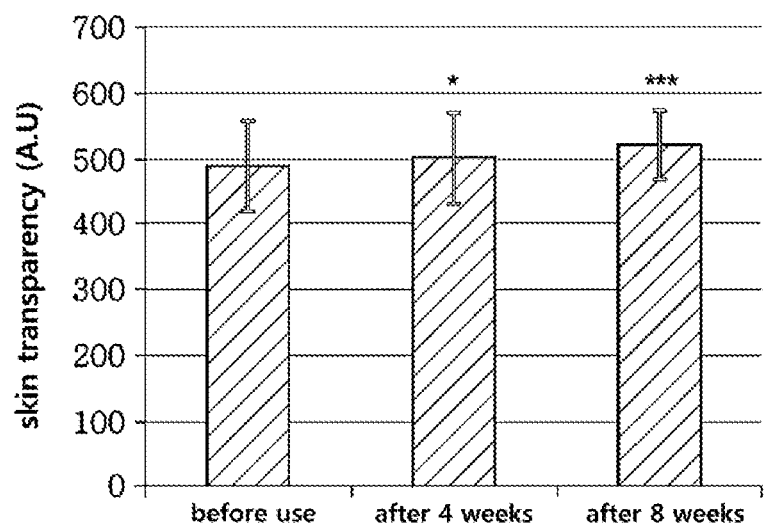
FIG. 4 shows the evaluation result of efficacy of the mixture extract on improving skin transparency according to one embodiment of the present disclosure (average ±SD; \*, p<0.05; \*\*\*, p<0.001 vs. before use).

The changes of skin transparency after the use of the test product for 8 weeks were analyzed by using the skin subsurface reflection value, and the results are shown in Table 2 and FIG. 4. As the result, it was verified that the average value of subsurface reflection was significantly increased after the use of the test product and thereby skin transparency was increased after 4 weeks and after 8 weeks. Thereby, it was confirmed that the mixture extract according to the specification of the present disclosure has the significant effect of improving skin transparency.

TABLE 2

| Parameter | week | mean | SD | p-value | increasing rate (%) |
|---|---|---|---|---|---|
| Transparency (A.U) | before use | 488.667 | 69.289 | — | — |
| | after 4 weeks | 501.333 | 68.245 | 0.012* | 2.592▲ |
| | after 8 weeks | 520.762 | 50.878 | 0.000*** | 6.568▲ |

(*p < 0.05; ***p < 0.001 vs. before the use)

The formulation examples of the composition according to one aspect of the specification of the present disclosure will be explained below, but the application of other several formulations is possible, and the examples does not intend to limit the present disclosure, but are just to specifically explain the present disclosure.

Formulation Example 1 Toner

Toner comprising the composition of Table 3 below was prepared according to the typical method.

TABLE 3

| Blending ingredients | Content (wt. %) |
|---|---|
| Mixture extract of Example 1 | 0.5 |
| Glycerin | 3.5 |
| Butylene glycol | 2.0 |
| Propylene glycol | 2.0 |
| Oleyl alcohol | 1.5 |
| Ethanol | 5.5 |
| Polysorbate 80 | 3.2 |
| Carboxyvinyl polymer | 0.1 |
| Preservative, color, spice | proper amount |
| Purified water | balance |
| Total | 100 |

Formulation Example 2 Lotion

Lotion comprising the composition of Table 4 below was prepared according to the typical method.

TABLE 4

| Blending ingredients | Content (wt. %) |
|---|---|
| Mixture extract of Example 1 | 0.5 |
| Glycerin | 3.0 |
| Butylene glycol | 3.0 |
| Propylene glycol | 3.0 |
| Carboxyvinyl polymer | 0.2 |
| Cera | 4.0 |
| Polysorbate 80 | 1.5 |
| Caprylic/capric Triglyceride | 5.0 |
| Squalane | 5.0 |
| Sorbitan sesquiolate | 1.5 |
| Cetearyl alcohol | 1.0 |
| Triethanolamine | 0.2 |
| Preservative, color, spice | proper amount |
| Purified water | balance |
| Total | 100 |

Formulation Example 3 Essence

Essence comprising the composition of Table 5 below was prepared according to the typical method.

TABLE 5

| Blending ingredients | Content (wt. %) |
|---|---|
| Mixture extract of Example 1 | 0.5 |
| Cetyl octanoate | 1.0 |
| Octyldodeceth-16 | 0.5 |
| Polyglyceryl-10 oleate | 0.2 |
| Polysiloxane | 0.4 |
| Tocopherol acetate | 0.1 |
| Ethanol | 6.0 |
| Glycerin | 15.0 |
| Xanthan gum | 0.07 |
| Propylene glycol | 4.0 |
| Carboxyvinyl polymer | 0.12 |
| Preservative, color, spice | proper amount |
| Purified water | balance |
| Total | 100 |

Formulation Example 4 Cream

Cream comprising the composition of Table 6 below was prepared according to the typical method.

TABLE 6

| Blending ingredients | Content (wt. %) |
|---|---|
| Mixture extract of Example 1 | 0.5 |
| Glycerin | 3.5 |
| Butylene glycol | 3.0 |
| Liquid paraffin | 7.0 |
| Beta-glucan | 7.0 |
| Carbomer | 0.1 |
| Caprylic/capric Triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Preservative, color, spice | proper amount |
| Purified water | balance |
| Total | 100 |

Formulation Example 5 Gel

Gel comprising the composition of Table 7 below was prepared according to the typical method.

TABLE 7

| Blending ingredients | Content (wt. %) |
|---|---|
| Mixture extract of Example 1 | 0.5 |
| Cetearyl glucoside | 1.5 |
| Cetyl octanoate | 1.0 |
| Glycerin | 5.0 |
| Jojoba wax | 3.0 |
| Dielpanthenol | 1.0 |
| Ethanol | 7.0 |
| Carboxyvinyl polymer | 0.6 |
| Propylene glycol | 3.0 |
| Preservative, color, spice | proper amount |
| Purified water | balance |
| Total | 100 |

Formulation Example 6 Pack

Pack comprising the composition of Table 8 below was prepared according to the typical method.

TABLE 8

| Blending ingredients | Content (wt. %) |
| --- | --- |
| Mixture extract of Example 1 | 0.5 |
| Glycerin | 4.0 |
| Polyvinyl alcohol | 15.0 |
| Hyaluronic acid extract | 5.0 |
| Beta-glucan | 7.0 |
| Allantoin | 0.1 |
| Propylene glycol | 3.0 |
| Polysorbate 60 | 1.2 |
| Preservative, color, spice | proper amount |
| Purified water | balance |
| Total | 100 |

While the present disclosure has been described with respect to the specific embodiments, it will be apparent to those skilled in the art that various changes and modifications may be made without departing from the spirit and scope of the disclosure as defined in the following claims.

The invention claimed is:

1. A method for improving skin transparency, comprising administering an effective amount of a mixture extract from *Rosa multiflora* fruit, black sesame, *Prunus mume* fruit, quince and pine nut for improving skin transparency to a subject in need thereof, wherein the *Rosa multiflora* fruit, black sesame, *Prunus mume* fruit, quince and pine nut are mixed at the weight ratios of 10 to 30:20 to 40:10 to 25:15 to 30:15 to 30, respectively, further wherein said skin transparency is a ratio of transmitted light to incident light on a skin surface.

2. A method for improving skin dullness, comprising administering an effective amount of a mixture extract from *Rosa multiflora* fruit, black sesame, *Prunus mume* fruit, quince and pine nut for improving skin dullness to a subject in need thereof, wherein the *Rosa multiflora* fruit, black sesame, *Prunus mume* fruit, quince and pine nut are mixed at the weight ratios of 10 to 30:20 to 40:10 to 25:15 to 30:15 to 30, respectively.

3. The method according to claim 2, wherein said *Rosa multiflora* fruit and black sesame are germinated *Rosa multiflora* fruit and germinated black sesame.

4. The method according to claim 2, wherein said extract is a solvent extract from at least one of water and lower alcohols having 1 to 4 carbon atoms.

5. The method according to claim 4, wherein said extract is an ethanol extract.

6. The method according to claim 2, wherein said extract is administered to a subject in one or more forms of a pharmaceutical composition, a skin external preparation composition, a food composition or a cosmetic composition, and the pharmaceutical composition, the skin external preparation composition, the food composition or the cosmetic composition comprises 0.001 to 20 wt. % of said mixture extract, respectively.

7. The method according to claim 6, wherein said cosmetic composition is in a toner, lotion, essence, cream, gel or pack formulation.

8. The method according to claim 2, wherein said mixture extract inhibits the generation of a substance exhibiting autofluorescence under the fluorescence conditions of 340 nm of excitation light and 440 nm of emission light.

9. The method according to claim 1, wherein said *Rosa multiflora* fruit and black sesame are germinated *Rosa multiflora* fruit and germinated black sesame.

10. The method according to claim 1, wherein said extract is a solvent extract from at least one of water and lower alcohols having 1 to 4 carbon atoms.

11. The method according to claim 10, wherein said extract is an ethanol extract.

12. The method according to claim 1, wherein said extract is administered to a subject in one or more forms of a pharmaceutical composition, a skin external preparation composition, a food composition or a cosmetic composition, and the pharmaceutical composition, the skin external preparation composition, the food composition or the cosmetic composition comprises 0.001 to 20 wt. % of said mixture extract, respectively.

13. The method according to claim 12, wherein said cosmetic composition is in a toner, lotion, essence, cream, gel or pack formulation.

14. The method according to claim 1, wherein, when measuring skin subsurface reflection values before and after the use of said mixture extract at incident angle 60° and reflection angle 60° on the skin surface, the increase rate of the skin subsurface reflection values is 2% or more as compared to before the use of the mixture extract.

* * * * *